(12) United States Patent
Missling

(10) Patent No.: US 10,933,062 B2
(45) Date of Patent: *Mar. 2, 2021

(54) ANALGESIC THERAPEUTIC AND METHOD, 1-(3-4(((1 R,3S,5S)-ADAMANTAN-1-YL)(PHENYL)METHYL)PROPYL)-4-METHYLPIPERAZINE AND SALTS THEREOF

(71) Applicant: ANAVEX LIFE SCIENCES CORP., New York, NY (US)

(72) Inventor: Christopher U. Missling, New York, NY (US)

(73) Assignee: ANAVEX LIFE SCIENCES CORP., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/267,102

(22) Filed: Feb. 4, 2019

(65) Prior Publication Data

US 2019/0167668 A1  Jun. 6, 2019

Related U.S. Application Data

(63) Continuation of application No. 15/340,311, filed on Nov. 1, 2016, now Pat. No. 10,195,192.

(51) Int. Cl.
*A61K 31/495* (2006.01)
*A61P 25/02* (2006.01)

(52) U.S. Cl.
CPC ............ *A61K 31/495* (2013.01); *A61P 25/02* (2018.01)

(58) Field of Classification Search
CPC .............................. A61K 31/495; A61P 25/02
See application file for complete search history.

(56) References Cited

U.S. PATENT DOCUMENTS

| 8,188,115 B2 | 5/2012 | Torrens Jover |
| 2004/0038874 A1 | 2/2004 | Omoigui |
| 2012/0302568 A1* | 11/2012 | Vela Hernandez .... A61K 31/00 514/236.5 |

OTHER PUBLICATIONS

Riganas et. al., Journal of Medicinal Chemistry, 2012, ACS, vol. 55, pp. 10241-10261 (Year: 2012).*
Berge, J. Pharmaceutical Sciences, 1977, vol. 66(1), pp. 1-19 (Year: 1977).*
Bennet GJ and Xie YK, "A peripheral mononeuropathy in rat that produces disorders of pain sensation like those seen in man," Pain (33), 87-107 (1998).
Randall LO and Selitto JJ, "A method for measurement of analgesic activity on inflamed tissue," Arch, Int. Pharmacodyn., 111, 409-419 (1957).
Gris et al., "The selective sigma-1 receptor antagonist E-52862 attenuates neuropathic pain of different aetiology in rats," Sci Rep. Apr. 18, 2016; 6:24591.
Riganas et al., "New adamantane phenylalkylamines with σ-receptor binding affinity and anticancer activity, associated with putative antagonism of neuropathic pain," J Med Cham. Nov. 26, 2012, 55(22): 10241-61.

* cited by examiner

*Primary Examiner* — Sarah Pihonak
(74) *Attorney, Agent, or Firm* — Polsinelli PC; Tara A. Nealey

(57) ABSTRACT

A method for the treatment and/or prevention of pain which comprises administering to a subject in need of such treatment a therapeutically effective amount of 1-(3-4(((1R,3S,5S)-adamantan-1-yl)(phenyl)methyl)propyl)-4-methylpiperazine and pharmaceutically acceptable salts thereof ("AV1066"), with reference to visceral and neuropathic pain.

21 Claims, 5 Drawing Sheets

ANALGESIC THERAPEUTIC AND METHOD, 1-(3-4(((1 R,3S,5S)-ADAMANTAN-1-YL)(PHENYL)METHYL)PROPYL)-4-METHYLPIPERAZINE AND SALTS THEREOF

CROSS REFERENCE TO RELATED APPLICATIONS

This application is a Continuation of U.S. patent application Ser. No. 15/340,311, filed Nov. 1, 2016, the entire disclosure of which is incorporated herein by reference in its entirety.

FIELD TO THE INVENTION

A method of treating nociceptive and neuropathic pain employing the analgesic and anti-hyperalgesic therapeutic properties of 1-(3-4(((1R,3S,5S)-adamantan-1-yl)(phenyl)methyl)propyl)-4-methylpiperazine and pharmaceutically acceptable salts thereof ("AV1066").

BACKGROUND OF THE INVENTION

Reference is made to 1-(3-4(((1R,3S,5S)-adamantan-1-yl)(phenyl)methyl)propyl)-4-methylpiperazine (ANAVEX™ 1066 or "AV1066") as presented below:

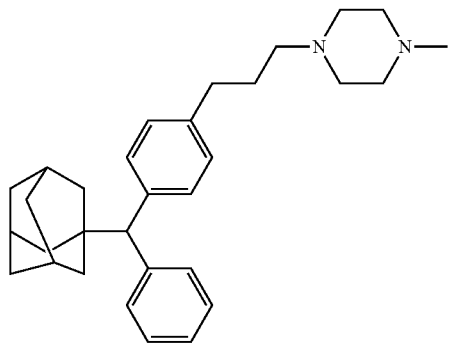

1-(3-(4-(((1R,3S,5S)-adamantan-1-yl)(phenyl)methyl)phenyl)propyl)-4-methylpiperazine AV 1066 is chiral, denoted as (+) 1-(3-4(((1R,3S,5S)-adamantan-1-yl)(phenyl)methyl)propyl)-4-methylpiperazine and salts thereof and (−) 1-(3-4(((1R,3S,5S)-adamantan-1-yl)(phenyl)methyl)propyl)-4-methylpiperazine and salts thereof. ANAVEX™ 1066 (AV1066), a mixed Sigma-1/Sigma-2 receptor ligand, has previously demonstrated antitumor activity as well as analgesic effects in animal models (Riganas et al., J. Med. Chem. 55:1041, 2012). AV1066 includes, without limitation, the free base and pharmaceutically acceptable salts such as sodium, ammonium, phosphate, hydrochloride, and mesylate.

Reference is made to the following publications, the teachings of which are incorporated herein in their entirety as are all publications cited here.
1. Bennett G J and Xie Y K, "A peripheral mononeuropathy in rat that produces disorders of pain sensation like those seen in man," *Pain*, (33), 87-107 (1988).
2. Randall L O and Selitto J J, "A method for measurement of analgesic activity on inflamed tissue," *Arch. Int. Pharmacodyn.*, 111, 409-419 (1957).
3. Gris et al., "The selective sigma-1 receptor antagonist E-52862 attenuates neuropathic pain of different aetiology in rats," *Sci Rep.* 2016 Apr. 18; 6:24591.
4. Riganas et al., "New adamantane phenylalkylamines with a-receptor binding affinity and anticancer activity, associated with putative antagonism of neuropathic pain," *J Med Chem.* 2012 Nov. 26; 55(22):10241-61.

Hyperalgesia is an increased sensitivity to pain, which in one form is caused by damage to nociceptors in the body's soft tissues. Anti-hyperalgesic is a property to reduce such pain sensitivity (i.e., a positive effect).

Visceral pain or nociceptive is pain that results from the activation of nociceptors of the thoracic, pelvic, or abdominal viscera (organs). Visceral structures are highly sensitive to distension (stretch), ischemia and inflammation, but relatively insensitive to other stimuli that normally evoke pain such as cutting or burning. Reported causative or associated events include sprains, bone fractures, burns, bumps, bruises, inflammation (from an infection or arthritic disorder), obstructions, and myofascial pain.

Neuropathic pain is a complex, chronic pain state that usually is accompanied by tissue injury. With neuropathic pain, the nerve fibers themselves may be damaged, dysfunctional, or injured. These damaged nerve fibers send incorrect signals to other pain centers. This is often associated with lesions or disease affecting the somatosensory nervous system either in the periphery or centrally. Reported causative factors for neuropathic pain include painful polyneuropathy, postherpetic neuralgia, trigeminal neuralgia, and post-stroke pain. Neuropathic pain is also understood to arise from cancer, a neurological disorder, spine or peripheral nerve surgery, a brain tumor, traumatic brain injury (TBI), spinal cord trauma, a chronic pain syndrome, fibromyalgia, chronic fatigue syndrome, a neuralgia, lupus, sarcoidosis, peripheral neuropathy, bilateral peripheral neuropathy, diabetic neuropathy, central pain, neuropathies associated with spinal cord injury, stroke, ALS, Parkinson's disease, multiple sclerosis, sciatic neuritis, mandibular joint neuralgia, peripheral neuritis, polyneuritis, stump pain, phantom limb pain, a bony fracture, oral neuropathic pain, Charcot's pain, complex regional pain syndrome I and II (CRPS III), radiculopathy, Guillain-barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia or vidian neuralgia.

SUMMARY OF THE INVENTION

This invention includes a method for the treatment and/or prevention of pain which comprises administering to a subject in need of such treatment a therapeutically effective amount of 1-(3-4(((1R,3S,5S)-adamantan-1-yl)(phenyl)methyl)propyl)-4-methylpiperazine and pharmaceutically acceptable salts thereof ("AV1066"). Particular reference is made to this method employing dosages of from about 1 mg/kg/day to about 250 mg/kg/day, as well as from about 5 mg/kg/day to about 50 mg/kg/day, and more particularly from about 10 mg/kg/day to about 30 mg/kg/day. Yet further reference is made to dosages of from about 250 mg/day to about 1000 mg/day, and more particularly from about 350 mg/day to about 750 mg/day. Dosing with the (+) form substantially absent the (−) form is noted. In specific embodiments dosing will be with the (−) form substantially absent the (+) form. "Substantially absent" shall be understood to mean no more than about 5% w/w and more preferably no more than 1% w/w.

In some embodiments the method is for the treatment of visceral pain comprising administering AV1066 in a dosage of from about 5 mg/kg/day to about 50 mg/kg/day, and particularly from about 10 mg/kg/day to about 30 mg/kg/day. Additional note is made of the method employing dosages of from about 250 mg/day to about 1000 mg/day and more particularly from about 350 mg/day to about 750 mg/day.

In other embodiments the method is for the treatment of neuropathic pain comprising administering AV1066 in a dosage of from about 5 mg/kg/day to about 50 mg/kg/day and particularly from about 10 mg/kg/day to about 30 mg/kg/day. Additional note is made of the method employing dosages of from about 250 mg/day to about 1000 mg/day and more particularly from about 350 mg/day to about 750 mg/day.

Note is made of the use of AV1066 administered in conjunction with a pharmaceutically acceptable carrier.

Results are expressed as mean±s.e.m. ; *: p<0.01 and 0.001, respectively as compared to the vehicle-treated group, Bonferroni's test after significant one way ANOVA.

DETAILED DESCRIPTION OF THE INVENTION

In evaluating AV1066, chronic constriction injury (CCI) was employed as a model of neuropathic pain (Bennett & Xie, Pain 33:87, 1988). Briefly, a loose ligature around the sciatic nerve was performed in rats, resulting in mechanical hyperalgesia in the ipsalateral hind limb as measured 14 days later. Single administration of AV1066 (10, 30, 100 mg/kg PO, n=10/group) produced a dose-dependent reduction in nociceptive threshold in the affected paw. Efficacy was apparent 30 minutes post-dose and remained significant for 2 hours, a time course comparable to the single SC dose of morphine that served as the positive control. In separate experiments, colonic hypersensitivity was induced by injection of TNBS (2,4,6-trinitrobenzenesulfonic acid) directly into the proximal end of the colon; 7 days later inflation of a balloon inserted into the distal end was employed to yield a painful response (Diop et al., *JPET* 302:1013, 2002). Single PO administration of AV1066 (n=10/group) returned the colorectal distention threshold to control levels within the same dose range as that used in the CCI model. U-50, 488H, a kappa agonist, served as the reference standard. No untoward effects of AV1066 were observed in either study.

AV1066 showed robust, dose-dependent efficacy in 2 different animal models of pain, the CCI model of neuropathic pain and the TNBS model of visceral pain, suggesting therapeutic potential in 2 distinct and poorly served patient populations.

Efficacy

Assessment of the efficacy of a single oral administration of AV1066 in a model of peripheral mononeuropathy (Bennett model) in rats The anti-hyperalgesic effect observed for the 30 mg/kg dose of AV1066 (at T=+30 minutes) is 59%. That is, the difference in the nociceptive threshold in animals dosed with AV1066 vs. those dosed with vehicle (312 g–196 g=116 g) divided by the threshold for the vehicle group (116 g/196 g=59%). The 59% observed anti-hyperalgesic effect compares favorably with non-opioid treatments such as gabapentin that typically range from 40-50%.

Without being bound by any particular theory, AV-1066 has a positive effect on the hypersensitivity likely due to the nerve constriction. At any moment, treated animals with AV-1066, whatever the dose, came back to values observed to the intact hind paw (max effect+59%).

Figure 1:
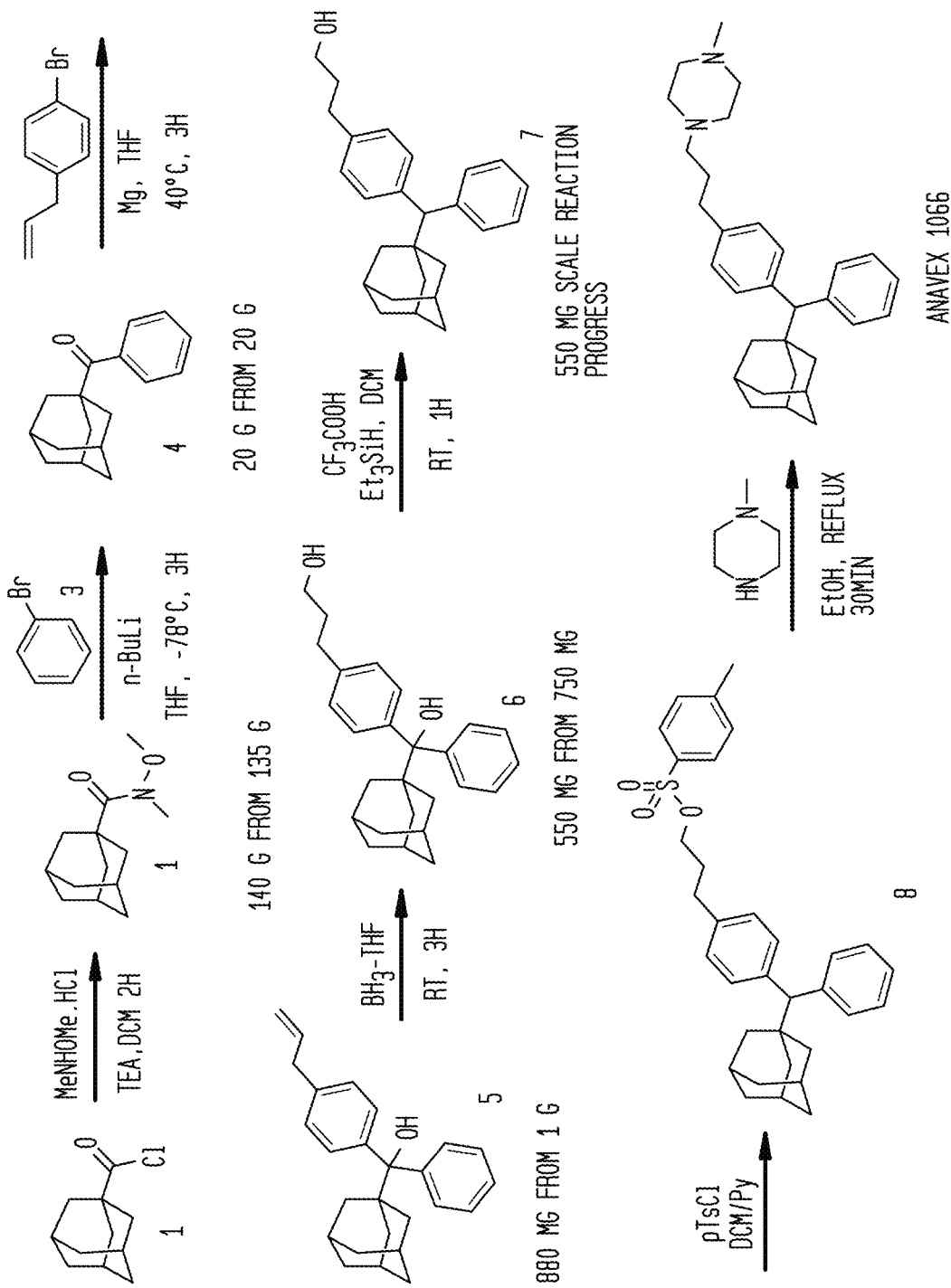
FIG. 1 is a schematic of the Synthesis of AV1066.
Figure 2:
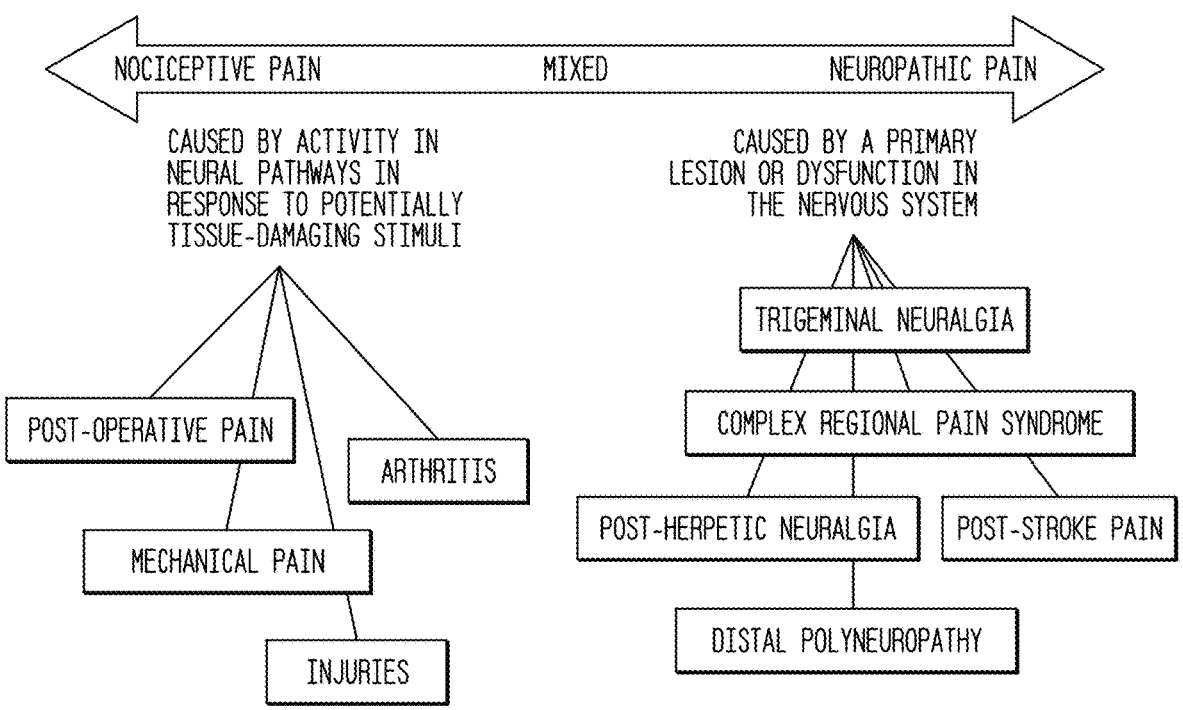
FIG. 2 is a conceptual representation of nociceptive or visceral pain as contrasted with neuropathic pain.
Figure 3:
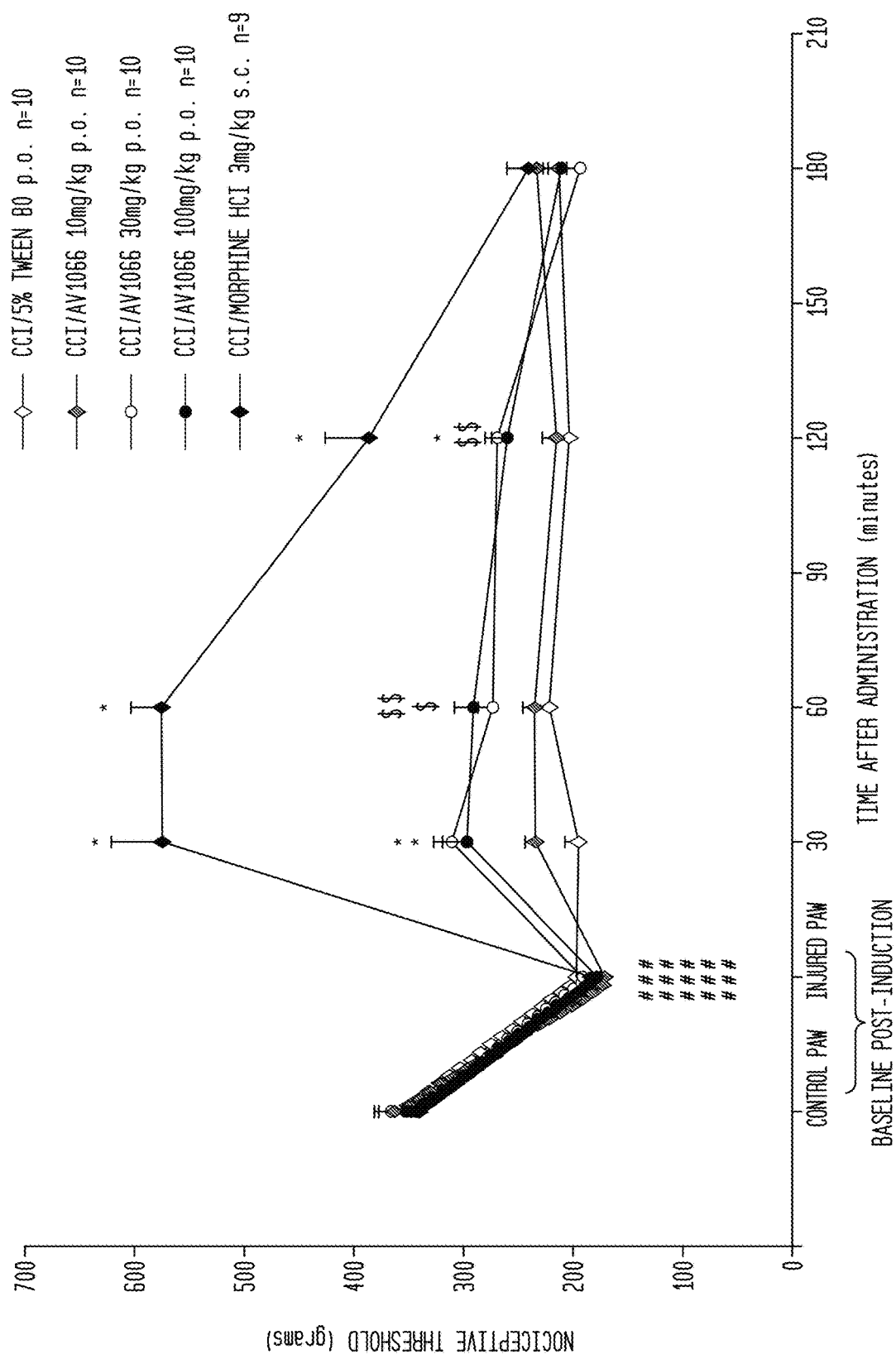
FIG. 3 is a graph of the effect of a single oral administration of AV1066 in a model of peripheral mononeuropathy (Bennett model) in rats.
Figure 4:
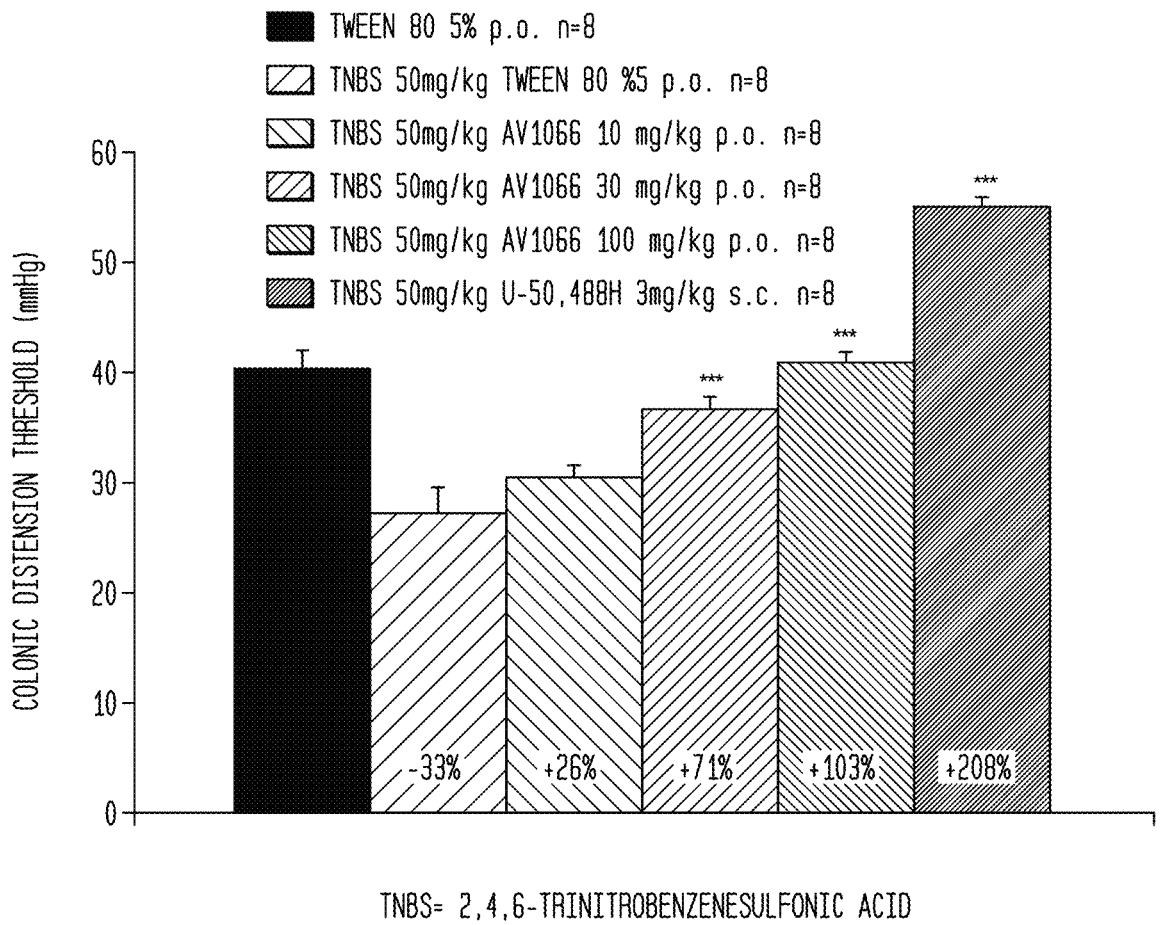
FIG. 4 is a bar graph testing AV1066 in TNBS-induced colonic hypersensitivity. AV1066 dose-dependently restores the colonic distention threshold lowered by pretreatment with TNBS. Here, colo-rectal distension results from TNBS-induced hypersensitivity. Progressive balloon inflation establishes numerical threshold for postural change.
Figure 5:
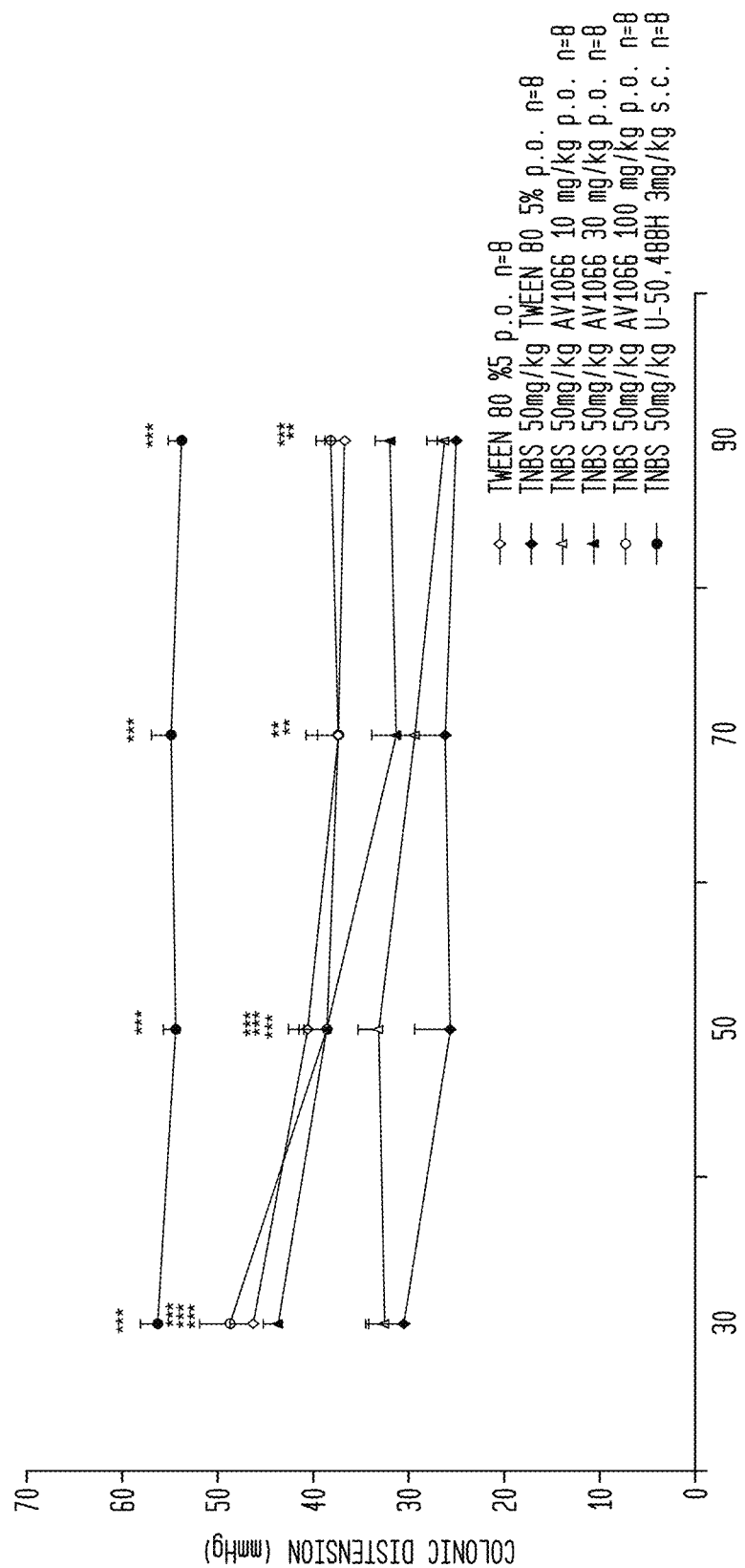
FIG. 5 is a graph of the effect of a single oral administration of AV1066 in the model of TNBS-induced chronic colonic hypersensitivity in rats.

The effect of a single oral administration of AV1066 in a model of peripheral mononeuropathy (Bennett model) in rats is shown in FIG. 3. These results are expressed as mean±s.e.m. ###: p<0.001, as compared to the control paw of the corresponding group: Mann-Whitney Rank Sum test. *: p<0.05 as compared to the vehicle-treated group, Dunn's test after significant Kruskal-Wallis ANOVA on ranks. $, $$: p<0.05 and p<0.01 as compared to the vehicle-treated group, Mann-Whitney Rank Sum test. In these results AV1066 dose-dependently restores the pain threshold lowered by chronic constriction injury. Here, chronic constriction injury consists of a loose ligation of the sciatic nerve under anesthesia with testing 14 days post-operative.

TABLE I

Effect of a single oral administration of AV1066 in a model of peripheral mononeuropathy (Bennett model) in rats.

| Control paw | T0 | | | | |
|---|---|---|---|---|---|
| Substance | 5% Tween 80 | AV1066 | AV1066 | AV1066 | Morphine HCl |
| Dose | — | 10 mg/kg | 30 mg/kg | 100 mg/kg | 3 mg/kg |
| Route of administration | p.o. | p.o. | p.o. | p.o. | sc. |
| Nociceptive threshold (g) | 366 ± 16.1 | 366 ± 11.9 | 352 ± 15.8 | 354 ± 9.9 | 349 ± 11.1 |
| n | 10 | 10 | 10 | 10 | 9 |
| Injured paw | | | | | |
| Substance | 5% Tween 80 | AV1066 | AV1066 | AV1066 | Morphine HCl |
| Dose | — | 10 mg/kg | 30 mg/kg | 100 mg/kg | 3 mg/kg |
| Route of administration | p.o. | p.o. | p.o. | p.o. | s.c. |

TABLE I-continued

Effect of a single oral administration of AV1066 in a model of peripheral mononeuropathy (Bennett model) in rats.

| | | | | | |
|---|---|---|---|---|---|
| Nociceptive threshold (g) | 200 ± 5.2 | 170 ± 11.6 | 192 ± 8.5 | 182 ± 9.6 | 184 ± 11.9 |
| % variation vs vehicle-treated group | — | −15% | −4% | −9% | −8% |
| % variation vs control paw | −45% | −54% | −45% | −49% | −47% |
| Statistical analysis | ### | ### | ### | ### | ### |
| | | | | | |
| Injured paw | T0 + 30 min | | | | |
| Substance | 5% Tween 80 | AV1066 | AV1066 | AV1066 | Morphine HCl |
| Dose | — | 10 mg/kg | 30 mg/kg | 100 mg/kg | 3 mg/kg |
| Route of administration | p.o. | p.o. | p.o. | p.o. | Sc. |
| | | | | | |
| Nociceptive threshold (g) | 196 ± 11.1 | 234 ± 11.2 | 312 ± 15.5 | 298 ± 21.4 | 576 ± 46.8 |
| % variation vs vehicle-treated group | — | 19% | 59% | 52% | 194% |
| % variation vs pre-drug threshold | −2% | 38% | 63% | 64% | 212% |
| % variation vs control paw | −36% | −32% | −19% | −20% | −11% |
| n | 10 | 10 | 10 | 10 | 9 |
| Statistical analysis | — | NS | * | * | * |
| | | | | | |
| Injured paw | T0 + 60 min | | | | |
| Substance | 5% Tween 80 | AV1066 | AV1066 | AV1066 | Morphine HCl |
| Dose | — | 10 mg/kg | 30 mg/kg | 100 mg/kg | 3 mg/kg |
| Route of administration | p.o. | p.o. | p.o. | p.o. | sc. |
| | | | | | |
| Nociceptive threshold (g) | 222 ± 13.5 | 236 ± 11.5 | 274 ± 14.3 | 292 ± 17.2 | 576 ± 28.8 |
| % variation vs vehicle-treated group | — | 6% | 23% | 32% | 159% |
| % variation vs pre-drug threshold | 11% | 39% | 43% | 60% | 212% |
| % variation vs control paw | −34% | −29% | −16% | −11% | −6% |
| n | 10 | 10 | 10 | 10 | 9 |
| Statistical analysis | — | NS | $ | $$ | * |
| | | | | | |
| Injured paw | T0 + 120 min | | | | |
| Substance | 5% Tween 80 | AV1066 | AV1066 | AV1066 | Morphine HCl |
| Dose | — | 10 mg/kg | 30 mg/kg | 100 mg/kg | 3 mg/kg |
| Route of administration | p.o. | p.o. | p.o. | p.o. | Sc. |
| | | | | | |
| Nociceptive threshold (g) | 204 ± 12.6 | 216 ± 12.6 | 270 ± 11.6 | 262 ± 12.5 | 387 ± 40.4 |
| % variation vs vehicle-treated group | — | 6% | 32% | 28% | 90% |
| % variation vs pm-drug threshold | 2% | 27% | 41% | 44% | 110% |
| % variation vs control paw | −43% | −30% | −21% | −23% | −11% |
| n | 10 | 10 | 10 | 10 | 9 |
| Statistical analysis | — | NS | * | $$ | * |
| | | | | | |
| Injured paw | T0 + 180 min | | | | |
| Substance | 5% Tween 80 | AV1066 | AV1066 | AV1066 | Morphine HCl |
| Dose | — | 10 mg/kg | 30 mg/kg | 100 mg/kg | 3 mg/kg |
| Route of administration | p.o. | p.o. | p.o. | p.o. | sc. |
| | | | | | |
| Nociceptive threshold (g) | 214 ± 9.0 | 234 ± 15.5 | 194 ± 13.0 | 212 ± 15.8 | 242 ± 19.0 |
| % variation vs vehicle-treated group | — | 9% | −9% | −1% | 13% |
| % variation vs pre-drug threshold | 7% | 38% | 1% | 16% | 31% |
| % variation vs control paw | −27% | −23% | −36% | −27% | −19% |
| n | 10 | 10 | 10 | 10 | 9 |
| Statistical analysis | — | NS | NS | NS | NS |

The Table 1 results are expressed as mean±s.e.m. Percentage of variation are expressed as increase (+) or decrease (−) as compared to the vehicle-treated group. ###: $p<0.001$, as compared to the control paw of the corresponding group: Mann-Whitney Rank Sum test. *: $p<0.05$ as compared to the vehicle-treated group, Dunn's test after significant Kruskal-Wallis ANOVA on ranks. $, $$: $p<0.05$ and $p<0.01$ as compared to the vehicle-treated group, Mann-Whitney Rank Sum test.

Mechanical Hyperalgesia/Paw Pressure Test—Rats Principle

The model of Chronic Constriction Injury (CCI) is based on a discrete peripheral nerve injury and can be related to post-traumatic/postsurgical neuropathic pain experienced by patients. Unilateral peripheral mononeuropathy is induced by loose ligation of the sciatic nerve of the right hind paw of the rat. Fourteen days later, nociceptive thresholds are measured using the paw pressure test. The Paw Pressure test requires the application of an increasing pressure onto both hind paws until the animal makes a stereotyped response (paw withdrawal or vocalization). This assay is widely used for revealing the potency of new analgesics in a model of peripheral neuropathic pain in conscious rats.

TABLE 2

Effect of oral administration of AV1066 in the mode of TNBS-induced chronic colonic hypersensitivity in rats.

| Reagent | — | TNBS 50 mg/kg | TNBS 50 mg/kg | TNBS 50 mg/kg | TNBS 50 mg/kg | TNBS 50 mg/kg |
|---|---|---|---|---|---|---|
| Substance | Tween 80 | Tween 80 | AV1066 | AV1066 | TNBS 50 mg/kg | U-50,488H |
| Dose | 5% | 5% | 10 mg/kg | 30 mg/kg | 100 mg/kg | 3 mg/kg |
| Route of Admin. | p.o. | p.o. | p.o. | p.o. | p.o. | p.o. |
| Colonic distension threshold (mmHg) | 40.3 ± 1.7 | 26.9 ± 2.6 | 30.3 ± 1.3 | 36.4 ± 1.3 | 40.8 ± 1.1 | 54.8 ± 1.0 |
| n | 8 | 8 | 8 | 8 | 8 | 8 |
| % variation vs. naïf | — | −33% | — | — | — | — |
| % antihypersensitivity activity | — | — | 26% | 71% | 103% | 208% |
| Statistical analysis | *** | — | NS | *** | *** | *** |

Results are expressed as mean ± s.e.m. Percentage of variation are expressed as decreases as compared to the naive animals and as antihypersensitivity activity.
*** $p < 0.001$ as compared to the vehicle-treated group, Bonferroni's test after significant one way ANOVA.

EXAMPLE 1

Bone Fracture Pain

An 18 year old male patient or subject (the terms are used interchangeably) presents with a fractured collar bone arising from a bicycling accident. He is complaining of significant shoulder pain. The patient's pain is classified according to the
International Association for the Study of Pain as nociceptive. He is orally administered AV1066 5 mg/kg/day. He is examined at days 3, 7, 16, and 28. At each visit the patient is assessed for pain control compared with the previous visit. The patient reports the pain to be both tolerable and improved at each visit.

EXAMPLE 2

Burn Pain

A 38 year old female patient presents with a second degree to her left thigh. She is complaining of significant pain. The patient's pain is classified according to the International Association for the Study of Pain as nociceptive. She is orally administered the phosphate salt of AV1066 10 mg/kg daily in two doses. She is examined at 12 hours, and daily thereafter for 4 days. At each visit the patient is assessed for pain control compared with the previous visit. The patient reports the pain to be both tolerable and improved at each visit.

EXAMPLE 3

Obstruction Pain

A 68 year old female patient presents with a benign tumor mass compressing her left shoulder causing movement pain. The patient's pain is classified according to the International Association for the Study of Pain as nociceptive. She is orally administered the sodium salt of AV1066 30 mg/kg/day in two doses. She is examined daily thereafter at 3, 7, and 28 days. At each visit the patient is assessed for pain control compared with the previous visit. The patient reports the pain to be both tolerable and improved at each visit.

EXAMPLE 4

Postherpetic Pain

A 70 year old male patient presents with postherpetic neuralgia arising from a shingles outbreak. He is experiencing lingering pain in the skin of his left shoulder extending over his left shoulder blade. The patient's pain is classified according to the International Association for the Study of Pain as neuropathic. He is orally administered (+) AV1066 10 mg/kg daily on days when the pain becomes significant. The patient reports the pain reduced and the outbreaks lessened din severity and duration.

EXAMPLE 5

Trigeminal Pain

A 52 year old female patient presents with trigeminal neuralgia. She is experiencing extreme, sporadic, sudden burning or shock-like facial pain in the areas of the face where the branches of the trigeminal nerve are distributed—lips, eyes, nose, scalp, forehead, upper jaw, and lower jaw. The pain episodes last from a few seconds to as long as two minutes. These attacks can occur in quick succession, in volleys lasting as long as two hours.

She is orally administered 350 mg of (−) AV1066. She takes one to three doses in a 12 hour period depending on the result. In most instances, one or two doses significantly reduce the frequency and severity of pain.

The pharmacologically active compositions of this invention can be processed in accordance with conventional methods of Galenic pharmacy to produce medicinal agents for administration to patients, e.g., mammals including humans.

The compositions of this invention can be employed in admixture with conventional excipients, i.e., pharmaceutically acceptable organic or inorganic carrier substances suitable for parenteral, or enteral (e.g., oral or inhalation) use which do not deleteriously react with the active compositions. Suitable pharmaceutically acceptable carriers include but are not limited to water, salt solutions, e.g., saline. The pharmaceutical preparations can be sterilized and if desired mixed with auxiliary agents, e.g., 1 salts for influencing osmotic pressure, buffers and the like which do not deleteriously react with the active compositions. They can also be combined where desired with other active agents, e.g., NSAID's.

Concerning NSAID as a combination medication with AV1066, there is considerable variability as to the presenting condition of subjects, the skilled practitioner is expected to adjust dosages in such regard. Nevertheless it is noted that indomethacin is particularly useful when contained in tablets of from about 25 to 75 mg. Also noted are ibuprofen doses of from about 50 to about 800 mg, flurbiprofen doses of about 100 to 500 mg; ketoprofen doses of about 100 to 500 mg; naproxen doses of about 100 to 1250 mg. Also noted is oxaprozin in doss of about 1200 mg to about 1800 mg or 26 mg/kg, etodolac doses of from about 200 to 1200 mg, ketorolac of from about 10 to about 150 mg, nabumetane doses of about 500 mg and 750 mg and 1500-2000 mg/day. In some instances mefenamic acid at from about 100 to about 1000 mg, meclofenamate sodium doses of about 50 mg up to about 400 mg, and piroxicam from about 10 to 50 mg.

In some embodiments of the present invention, dosage forms include instructions for the use of such compositions.

For parenteral application, particularly suitable are injectable, sterile solutions, preferably oily or aqueous solutions, as well as suspensions, emulsions, or implants, including suppositories. Ampules are convenient unit dosages.

Sustained or directed release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

Generally, the compositions of this invention are dispensed in unit dosage form comprising about 1 to about 100 mg in a pharmaceutically acceptable carrier per unit dosage.

The dosages of the compositions according to this invention generally are 1 to 100 mg/kg/day, preferably 1 to 10 (especially if the general dosage range spans an order of magnitude or more). Particular reference is made to doses of about 5 mg to about 50 mg/kg/day, and particularly doses of about 10 mg to about 30 mg/kg/day, and more particularly of from about 15 mg to about 250 mg/kg/day. Unit dosage forms of from about 250 mg to about 1 g are noted with particular reference to dosage forms of from about 350 mg to about 750 mg.

It will be appreciated that the actual preferred amounts of active compositions in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

The terms "effective amount" or "therapeutically effective amount" as used herein, refer to a sufficient amount of at least one agent being administered which achieves a desired result, e.g., to relieve to some extent one or more symptoms of a disease or condition being treated. In certain instances, the result is a reduction and/or alleviation of the signs, symptoms, or causes of a disease, or any other desired alteration of a biological system. In certain instances, an "effective amount" for therapeutic uses is the amount of the composition comprising an agent as set forth herein required to provide a clinically significant decrease in a disease. An appropriate "effective" amount in any individual case is determined using any suitable technique, such as a dose escalation study.

The compounds in accordance with the present invention are beneficial in the treatment and/or prevention of various human ailments. These include autoimmune and inflammatory disorders; neurological and neurodegenerative disorders; pain and nociceptive disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, polymyositis, scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behcet's disease and Sjogren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy) and organ transplant rejection (including kidney allograft rejection).

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

What is claimed is:

1. A method for the treatment and/or prevention of pain, the method comprising administering to a subject in need thereof a therapeutically effective amount of 1-(3-(4-(((1R,3S,5S)-adamantan-1-yl)(phenyl)methyl)propyl)-4-methylpiperazine and pharmaceutically acceptable salts thereof ("AV1066"), wherein the AV1066 is in the (−) form substantially absent the (+) form.

2. The method of claim 1, comprising administering the AV1066 in a dosage of from about 5 mg/kg/day to about 50 mg/kg/day.

3. The method of claim 2, wherein the dosage is from about 10 mg/kg/day to about 30 mg/kg/day.

4. The method of claim 1, comprising administering the AV1066 in a dosage of from about 250 mg/day to about 1000 mg/day.

5. The method of claim 4, wherein the dosage is from about 350 mg/day to about 750 mg/day.

6. The method of claim 1, wherein the pain is nociceptive pain.

7. The method of claim 2, wherein the pain is visceral pain and the method comprises administering AV1066 in a dosage of from about 5 mg/kg/day to about 50 mg/kg/day.

8. The method of claim 7, wherein the dosage is from about 10 mg/kg/day to about 30 mg/kg/day.

9. The method of claim 1, wherein the pain is visceral pain and the method comprises administering AV1066 in a dosage of from about 250 mg/day to about 1000 mg/day.

10. The method of claim 9, wherein the dosage is from about 350 mg/day to about 750 mg/day.

11. The method of claim 1, wherein the pain is neuropathic pain and the method comprises administering AV1066 in a dosage of from about 5 mg/kg/day to about 50 mg/kg/day.

12. The method of claim 11, wherein the dosage is from about 10 mg/kg/day to about 30 mg/kg/day.

13. The method of claim 1, wherein the pain is neuropathic pain and the method comprises administering AV1066 in a dosage of from about 250 mg/day to about 1000 mg/day.

14. The method of claim 13, wherein the dosage is from about 350 mg/day to about 750 mg/day.

15. The method of claim 1, wherein the pain is hyperalgesia pain and the method comprises administering AV1066 in a dosage of from about 5 mg/kg/day to about 50 mg/kg/day.

16. The method of claim 15, wherein the dosage is from about 10 mg/kg/day to about 30 mg/kg/day.

17. The method of claim 1, wherein the pain is hyperalgesia pain and the method comprises administering AV1066 in a dosage of from about 250 mg/day to about 1000 mg/day.

18. The method of claim 17, wherein the dosage is from about 350 mg/day to about 750 mg/day.

19. The method of claim 1, wherein the AV1066 is in the sodium salt form.

20. The method of claim 1, wherein the AV1066 is in the phosphate salt form.

21. The method of claim 1, wherein the administration of the AV1066 comprises administering the AV1066 with a pharmaceutically acceptable carrier.

* * * * *